United States Patent
Msika et al.

(10) Patent No.: US 7,638,149 B2
(45) Date of Patent: Dec. 29, 2009

(54) PEPTIDE EXTRACT OF LUPINE AND PHARMACEUTICAL OR COSMETIC OR NUTRITIONAL COMPOSITION COMPRISING SAME

(75) Inventors: Philippe Msika, Paris (FR); Antoine Piccirilli, Epernon (FR); Francois Paul, Toulouse (FR)

(73) Assignee: Laboratoires Expanscience, Courbevoie (FR)

( * ) Notice: Subject to any disclaimer, the term of this patent is extended or adjusted under 35 U.S.C. 154(b) by 5 days.

(21) Appl. No.: 10/985,988

(22) Filed: Nov. 12, 2004

(65) Prior Publication Data
US 2005/0148498 A1 Jul. 7, 2005

Related U.S. Application Data

(63) Continuation of application No. 09/958,092, filed as application No. PCT/FR00/01007 on Apr. 18, 2000, now abandoned.

(30) Foreign Application Priority Data
Apr. 19, 1999 (FR) .................................. 99 04875

(51) Int. Cl.
*A61K 36/00* (2006.01)
(52) U.S. Cl. ...................... 424/776; 424/725
(58) Field of Classification Search .................. None
See application file for complete search history.

(56) References Cited

U.S. PATENT DOCUMENTS

| | | | | |
|---|---|---|---|---|
| 2,051,017 | A | * | 8/1936 | Schwarz et al. ................ 426/44 |
| 2,615,905 | A | * | 10/1952 | Forstmann et al. ........... 426/629 |
| 4,402,874 | A | * | 9/1983 | Johnson et al. .............. 530/377 |
| 6,039,962 | A | * | 3/2000 | Cauwet-Martin et al. ... 424/401 |
| 6,630,163 | B1 | * | 10/2003 | Murad ......................... 424/464 |
| 6,703,490 | B1 | * | 3/2004 | Perrier et al. ................ 530/402 |

FOREIGN PATENT DOCUMENTS

| | | | |
|---|---|---|---|
| DE | 19640992 | * | 4/1997 |
| FR | 2778565 | * | 11/1999 |
| JP | 10-007518 | | 1/1998 |
| JP | 2000026272 | * | 1/2000 |

OTHER PUBLICATIONS

Publication entitled "Croda launches plant complexes", Manuafacturing Chemist, Jun. 1998, p. 41, Promt Abstract enclosed.*
Ballester et al., J. Agric. Food Chem., 1980, vol. 28, No. 2, pp. 402-405, Abstract.
Gulewicz et al., Acta Microbiologica Polonica, 1994, vol. 43, No. 1, pp. 73-77, Abstract.
Hines, M. et al., "Screening for Cysteine Proteinase Inhibitor Activity in Legume Seeds." *Journal of the Science of Food and Agriculture*, vol. 59, pp. 555-557, Elsevier Applied Science Publishers, Barking, Great Britain, 1992.
Pothier et al., Journal of Pharmacy and Pharmacology, Aug. 1998, vol. 50, No. 8, pp. 949-954, Abstract.
Radlowski, M. et al., "Systemin-an Inducer of Proteinase Inhibitor Synthesis Can be Responsible For Biological Activity of a Luppin Extract Against Insects." *Journal of Plant Physiology*, vol. 150, pp. 220-223 Fischer, Stuttgart, Germany, 1997.
Silva et al., Ciencia e Pratica, 1995, vol. 19, No. 4, pp. 420-424, Abstract.
Croda International, Online Product Summary Hydrosesame AA, http://www.croda.co.uk/home.aspx?Page=2&view=dtl&d=content&s=53&r=68&p=846&prodName=&prodINCI=amino%20acid&prodGeneral=&prodApp=&prodID=311, Jan. 2, 2009 (1 pg).

* cited by examiner

*Primary Examiner*—Christopher R. Tate
(74) *Attorney, Agent, or Firm*—Foley & Lardner LLP

(57) ABSTRACT

A composition comprising a hydrolyzed peptide extract of a lupin and a method of producing the same.

26 Claims, 1 Drawing Sheet

Figure 1:
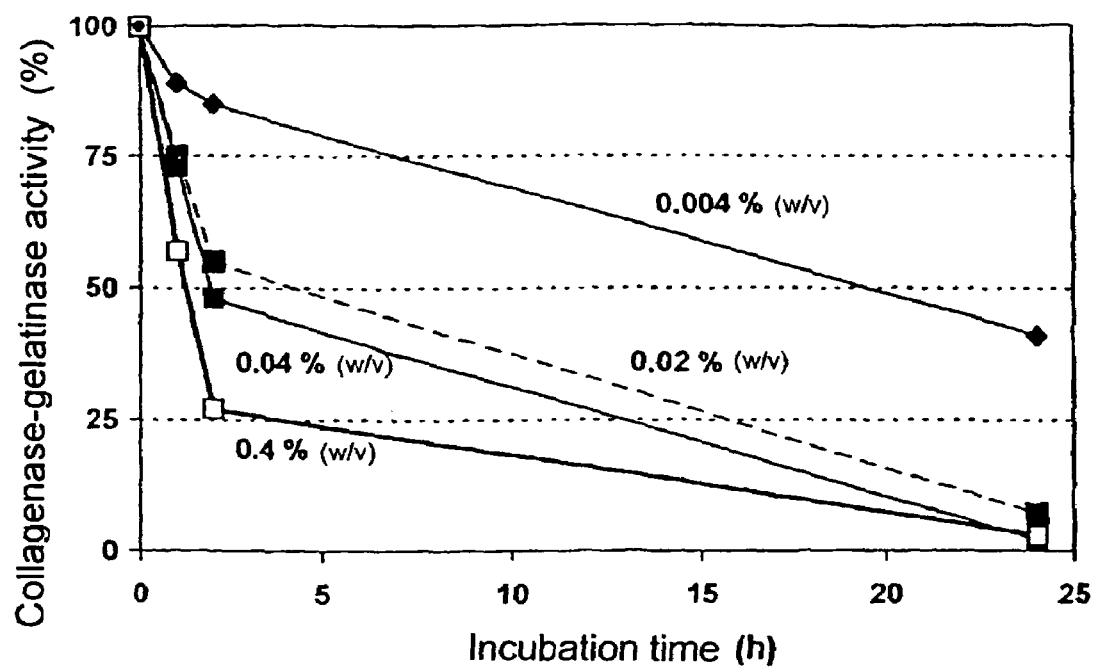

PEPTIDE EXTRACT OF LUPINE AND PHARMACEUTICAL OR COSMETIC OR NUTRITIONAL COMPOSITION COMPRISING SAME

The present invention relates to a novel peptide extract which has antimetalloprotease activity, in particular anticollagenase and antigelatinase activity. It also relates to the pharmaceutical, cosmetic or nutraceutical compositions comprising such an extract, in particular to a pharmaceutical composition intended to treat inflammatory diseases, such as arthrosis, parodontosis or ulcers, or to the cosmetic compositions intended to combat aging, which may or may not be actinic aging, or aging accelerated by outside attacks (tobacco, pollution, etc.).

The pharmaceutical, cosmetic or nutraceutical composition is also intended to treat neoangiogenesis (vessel proliferation) which is pathological or unsightly (psoriasis, tumors, erythosis, acne erythematosa, rosacea, local treatment with irritants such as retanoic acid), cicatrization deficiencies, burns or the attack of dental enamel (Ch. M. Lapiere, Cours de biologie de la peau [Skin biology course]—COBIP INSERM U 346, Lyon 1999).

Metalloproteases are a family of zinc- and calcium-dependent endopeptidases which have the combined property of degrading the diverse components of connective tissue matrices (thesis by S. Charvat—Métalloprotéinases et épiderme [Metalloproteinases and epidermis], pages 101-113 No. 248-98, 1998, Lyon I).

They are classified according to the nature of their substrate: collagenase (fibrillar collagen: ex. MMP-1, -13, -8); gelatinase (denaturated collagen, gelatin: ex. MMP-2, MMP-9); stromelysins (fibronectin, proteoglycin: ex. MMP-3, MMP-10). They are used in the physiological remodeling (low expression) or pathological remodeling of the extracellular matrix (strong induction).

Metalloproteases are in particular involved in the cicatrization process, eliminating the damaged tissues.

MMPs may act anarchically and cause significant lesions if their activity is not controlled.

Moreover, it is known that metalloproteases are involved in certain biological disorders, such as inflammatory diseases, in particular arthrosis and parodontosis (H. BIRKEDAL-HANSEN et al., *Critical Reviews in Oral Biology and Medicine*, 4(2): 197: 250 (1993)), in the processes of aging, in particular linked to the action of solar radiation (MARTIN RIEGER; Allured's Cosmetics & Toiletries®, Vol. 114, No. 1/January 1999 or G. J. FISHER et al., *The New England Journal of Medicine*, Vol. 337, No. 20 pp. 1419-1428, "Pathophysiology of premature skin aging induced by ultraviolet light" and G. J. FISHER et al., the *Society for Investigative Dermatology*, Inc. 1998, pp. 61-68 "Molecular mechanisms of photoaging and its prevention by retinoic acid: ultraviolet irradiation induces MAP kinase signal transduction cascades that induce A-1-regulated matrix metalloproteinases that degrade human skin in vivo") or in acute and chronic inflammations (XIE et al.; *J. Biol. Chem.* 273: pp. 11576-11582; 1998) and blistering diseases (toxic epidermal necrolysis), pathologies with cellular hyperproliferation during inflammation or irritation, bedsores, burns and ulcers.

The same is true for the proliferation of neoangiogenesis endothelial cells which, in their proliferative phase during inflammatory or pathological processes (psoriasis, tumors) need MPPs to destroy the connective tissue, in order to migrate toward other regions and to form microtubules and capillaries (*Controlling the vasculature: angiogenesis, anti-angiogenesis and vascular targeting of gene therapy*—T. P. D. FAN, R. JAGGAR and R. BICKNELL, TiPS—February 1995, Vol. 16; *Natural Products as angiogenesis inhibitors*, D. H. PAPER, *Planta Medical* 64 (1998) pp. 686-695; *Membrane-type matrix metalloproteinases in human dermal microvascular endothelial cells: expression and morphogenetic correlation*—V. T. CHAN et al., J.I.D. 111, pp. 1153-1159, 1998; *Matrix metalloproteinases in blood vessel development in human fetal skin and in cutaneous tumors*—T. V. KARELINA et al. J.I.D.; 105, 411-417, 1995; *Vascular profiferation and angiogenic factors in psoriasis*, J. D. CREAMER and J. N. W. N. BARKER, *Clinical and Experimental Dermatology*, 1995, 20, pp. 6-9).

The role of inhibitors of metalloproteases, in particular of collagenases, gelatinases and of stromelysins, in certain treatments for the abovementioned diseases is also known.

The object of the present invention is to provide a novel broad-spectrum inhibitor of metalloproteases of the collagenase or gelatinase type, which allows the treatment of humans or of mammals suffering from a condition or a disease linked to excess or pathological degradation of collagen or of another extracellular support macroprotein, or any other diseases linked to excessive expression of these proteolytic enzymes.

A subject of the invention is a peptide extract of lupin (*lupinus*), characterized in that it has activity for inhibiting metalloproteases, in particular collagenases or gelatinases. As a variety of lupin, mention is made in particular of the sweet white lupin genus (*lupinus albus*), such as the Ares variety which has a low alkaloid content.

A subject of the invention is in particular a novel peptide extract of lupin (*lupinus*), characterized in that it has an activity for inhibiting purified *Clostridium histolycum* collagenase on DQ-gelatin, which is in particular greater than 50% at 24 hours, for a concentration of equal to or greater than 0.1% (w/v).

According to one variant, this peptide extract of lupin is lipid-depleted.

It advantageously comprises at least 50%, preferably at least 70%, preferably at least 80% of peptide.

These peptides are obtained by hydrolysis of the protein fraction of lupin.

The hydrolysis may be carried out by any suitable means, in particular enzymatic hydrolysis.

A process for preparing such a peptide extract of lupin comprises the following steps:

preparing a lipid-free, ground lupin meal or a micronized lupin flour (containing lipid), extracting the soluble protein and saccharide fractions or precipitating with acid pH (4 or 5) depending on the isoelectric point, optionally separating the protein fraction, hydrolyzing the protein fraction and recovering, optionally after filtration, the protein extract.

The invention also relates to the protein extract which can be obtained using the abovementioned process.

In general, the invention comprises the lipid-containing lupin flours and the peptide extracts also comprising the sugars.

Preferably, the protein extract has the following amino acid composition (percentage by weight relative to the total weight of amino acids).

| Amino acids | %/total AAs |
|---|---|
| ASP | 11.3 |
| GLU | 23.2 |
| SER | 5.1 |
| HIS | 1.7 |
| GLY | 3.4 |
| THR | 3.2 |
| ALA | 2.8 |
| ARG | 10.3 |
| TYR | 6.1 |
| CYS-CYS | 2.4 |
| VAL | 3.8 |
| MET | 0.2 |
| PHE | 7.0 |
| ILE | 3.3 |
| LEU | 7.9 |
| LYS | 3.7 |
| PRO | 4.4 |

A subject of the invention is also a pharmaceutical, cosmetic or nutraceutical composition comprising a peptide extract as described above and, optionally, a suitable physiologically acceptable inert vehicle.

Such a pharmaceutical or dermocosmetic and nutraceutical composition is intended in particular for treating humans or mammals suffering from a condition or disease linked to excessive destruction of collagen and/or excessive destruction of support tissues. Such a composition may be used by way of prevention or cure.

Among these conditions or diseases, mention is made, for example, of arthrosis, periodontal diseases, diseases linked to skin lesions, inflammatory diseases, tumor-related or pathological neoangiogenesis (erythrosis, acne erythematosa, telangiectasia, rosacea, psoriasis, etc.), cicatrization deficiency, ulcers, burns, blistering diseases and the attack of dental enamel.

The invention also relates to cosmetic compositions for treating skin lesions due to aging, such as lesions caused by the action of solar radiation (photoaging), the intrinsic deleterious effects of the skin or the deleterious effects of tobacco.

The pharmaceutical, dermocosmetic or cosmetic compositions are, according to one variant, in the form of a formulation for topical application. A subject of the invention is therefore a method for cosmetic treatment, comprising applying such a composition on the surface of the skin of an individual.

The peptide extract according to the invention may also be incorporated into or formulated in a polymeric vehicle or a delivery system, for topical or local use, such as in the case of treating a periodontal disease, so as to be delivered directly into the periodontal pocket.

According to another variant, the pharmaceutical compositions are in the form of a formulation for oral administration.

These compositions may, in general, be formulated in the form of tablets, of capsules or of ointment.

In the case of nutraceutical compositions or food compositions, the forms conventionally used may be employed.

The invention is now illustrated using the examples of implementation described hereinafter, by way of illustration.

I—Preparation of Peptide Extracts of Lupin

I.1.—Extract A

Extraction and Purification of Lupin Proteins

This step comprises aqueous solubilization of the fraction soluble at alkaline pH, followed by separation from the insoluble components:

Using the lipid-free ground lupin meal, the proteins are extracted at pH 9.0 (pH adjusted by adding sodium hydroxide) with a flour/water ratio equal to 1/10 (w/w). The solution is incubated with stirring at room temperature for one hour. The insoluble portion of the meal is then separated from the soluble portion by spin-drying. The cake obtained is washed. The soluble fraction containing the soluble sugars and proteins is diafiltered on an ultrafiltration module with a cutoff threshold of 10 000 Daltons, in order to separate the proteins (retentate) from the soluble sugars (ultrafiltrate).

Production and Purification of Peptides by Enzymatic Hydrolysis:

The ultrafiltration retentate containing the proteins is adjusted to the concentration of 100 g/l and then hydrolyzed at pH 8.0 in the presence of Alcalase® (NOVO NORDISK) at 55° C. for approximately 3 h. After hydrolysis, the enzyme is denatured by hydrolysis for 15 min at 85° C. As soon as the solution has cooled down, it is neutralized by adding hydrochloric acid. The peptides obtained are purified by diafiltration on an ultrafiltration module with a cutoff threshold of 10 000 Daltons. The solution obtained is then nanofiltered in order to desalify (eliminate the sodium chloride) and concentrate the peptide fraction. The peptide solution is finally decolorized using 3% active charcoal (1 hour at 50° C.), the charcoal being removed by filtration.

Sterilization and Packaging of the Peptide fraction:

Before packaging, the solution is microfiltered (0.2 µm) sterilely and then distributed into sterile containers at the concentration of 10%, in the presence of preserving agents.

I.2—Extract B

The peptide extract B is obtained according to the described method implemented for obtaining extract A, except that the decolorization step is deleted.

I.3—Extract C

The peptide extract of lupin C is obtained according to the described method implemented for obtaining extract A, except that the purification, ultrafiltration and decolorizing steps are deleted.

II—Analysis of Peptide Extract A

The dry extract is then analyzed.

Presentation:

Appearance: nonhygroscopic homogeneous powder
Color: off-white
Amount: 5 g
Chemical composition:

| | |
|---|---|
| Total of sugar content (test using anthrone): | <1% |
| Chloride content (SIGMA kit ref: 955-30): | 6% |
| Water content (100° C., 4 h): | 8% maximum |
| Peptide content: | 85% |

Characterization

| | |
|---|---|
| pH (solution at 20 g/l): | 7.06 |
| Solubility (osmozed water) | >100 g/l |

TABLE 1

Amino acid composition of the hydrolysate

| Amino acids | M.W. A.A. | Conc. in mM | Conc. in mg/l | % in powder | %/total AAs |
|---|---|---|---|---|---|
| ASP | 133.1 | 2.078 | 276.582 | 9.9 | 11.3 |
| GLU | 147.1 | 3.858 | 567.438 | 20.3 | 23.2 |
| SER | 105.1 | 1.196 | 125.647 | 4.5 | 5.1 |
| HIS | 155.2 | 0.270 | 41.904 | 1.5 | 1.7 |
| GLY | 75.1 | 1.114 | 83.624 | 3.0 | 3.4 |
| THR | 119.1 | 0.664 | 79.023 | 2.8 | 3.2 |
| ALA | 89.1 | 0.763 | 67.983 | 2.4 | 2.8 |
| ARG | 174.2 | 1.447 | 251.980 | 9.0 | 10.3 |
| TYR | 181.2 | 0.829 | 150.215 | 5.4 | 6.1 |
| CYS-CYS | 240.3 | 0.247 | 59.234 | 2.1 | 2.4 |
| VAL | 117.1 | 0.792 | 92.743 | 3.3 | 3.8 |
| MET | 149.2 | 0.029 | 4.327 | 0.2 | 0.2 |
| PHE | 165.2 | 1.044 | 172.469 | 6.2 | 7.0 |
| ILE | 131.2 | 0.621 | 81.410 | 2.9 | 3.3 |
| LEU | 131.2 | 1.481 | 194.307 | 6.9 | 7.9 |
| LYS | 146.2 | 0.626 | 91.448 | 3.3 | 3.7 |
| PRO | 115.1 | 0.935 | 107.619 | 3.8 | 4.4 |
| Total |  |  | 2447.952 | 87.4% |  |

III—Anticollagenase and Antigelatinolytic Activity of the Lupin Peptides—Extract A, In Vitro The anticollagenase activity was measured in vitro in a biochemical model of the screening type, based on the use of a purified collagenase and of the substrate for the latter, gelatin conjugated to fluorescein (EnzChek™ gelatinase/collagenase kit, MOLECULAR PROBES). The collagenase purified from *Clostridium histolyticum* was supplied in the EnzChek™ gelatinase/collagenase kit (MOLECULAR PROBES). This enzymes has a double functionality on collagen IV (epidermis/dermis basal membrane) and gelatin.

The DQ-gelatin purified from porcine skin and conjugated to fluorescein was supplied in the EnzChek™ gelatinase/collagenase kit (MOLECULAR PROBES).

The reaction buffer, consisting of 0.05 M of Tris-HCl, 0.15 M NaCl, 5 mM of $CaCl_2$, and 0.2 mM of sodium azide (pH 7.6) was supplied in the EnzChek™ gelatinase/collagenase kit (MOLECULAR PROBES).

The peptide extract was solubilized in the reaction buffer. It was tested at 0.004; 0.02; 0.04; 0.2 and 0.4% (w/v).

The dilutions of the test extracts were incubated with DQ-gelatin at 1 mg/ml and collagenase at 0.2 Ru/ml for 1 hour, 2 hours and 24 hours at room temperature.

A control, corresponding to the "collagenase+DQ-gelatin" mixture, was incubated in parallel.

For each experimental condition, samples, subsequently named "samples without enzyme", were incubated in the presence of DQ-gelatin and in the absence of collagenase.

Each experimental condition was performed in triplicate.

After 1 hour, 2 hours and 24 hours, the signal corresponding to the degradation of the DQ-gelatin was measured by fluorimetry (excitation: 485 nm and emission: 595 nm). For each sample, the value obtained for the "samples without enzyme" was attracted.

The results were expressed as fluorescence units per sample and as percentage variation relative to the control group.

The groups of data (control group and treated groups) were compared by factor analysis of variance (ANOVA 1, $p<0.05$), followed by a Dunnett's test. The effect of the extracts was thus compared to that obtained in the control group.

The peptide extract tested from 0.004 to 0.2% (w/v) had a dose-dependent anticollagenase and antigelatinolytic activity. The effect was maximal at the 24 hour time point, as indicated in Table 2 below.

TABLE 2

| Control | 0.004 | 0.02 | 0.04 | 0.2 | 0.4 |
|---|---|---|---|---|---|
| Incubation time = 1 hour | | | | | |
| 16237 | 14161 | 11890 | 11205 | 11249 | 9434 |
| 14329 | 13561 | 11161 | 10863 | 9840 | 7544 |
| 15636 | 13965 | 11757 | 11344 | 11387 | 8878 |
| 15401 +/− 976 | **13896* +/− 306** | **11603* +/− 388** | **11137* +/− 248** | **10825* +/− 856** | **8619* +/− 971** |
| 100% | 89 | 75 | 73 | 73 | 57 |
| Incubation time = 2 hours | | | | | |
| 24776 | 20526 | 13689 | 11000 | 7617 | 6853 |
| 22516 | 19597 | 6710 | 10406 | 6072 | 4933 |
| 23779 | 20144 | 13148 | 11349 | 7824 | 6467 |
| 23690 +/− 1133 | **20089* +/− 467** | **11182* +/− 3883** | **10918* +/− 477** | **7171* +/− 957** | **6084* +/− 1016** |
| 100% | 85 | 55 | 48 | 33 | 27 |
| Incubation time = 24 hours | | | | | |
| 31653 | 12655 | 2583 | 2378 | 524 | 1154 |
| 29536 | 11531 | 1487 | 1442 | 484 | 467 |
| 29745 | 13008 | 2657 | 2713 | 693 | 927 |
| 30311 +/− 1167 | **12398* +/− 771** | **2242* +/− 655** | **2178* +/− 659** | **567* +/− 111** | **849* +/− 350** |
| 100% | 41 | 7 | 7 | 2 | 3 |

The results are expressed as fluorescence units/sample.
In bold: mean and standard deviation
*mean significantly different from the control group ($p < 0.05$).

In conclusion, under the experimental conditions selected, the protein extract tested between 0.004 and 0.4% (w/v) had a dose-dependent antigelatinase/collagenase activity. An excellent effect/dose/time ratio for the lupin peptides compared to the aspecific collagenase is in particular noted: at 24 hours, for example, 0.04% inhibits 93% of the gelatinolytic activity of the *clostridium* collagenase, at 2 hours: 52%.

Other tests with the same peptide extract were carried out at concentrations of 0.01; 0.05; 0.1; 0.5 and 1% (w/v) and the results are given in table 3 below and also in the attached FIG. 1. This figure represents the kinetics of inhibition of the aspecific collagenase—influence of the concentration of peptide extract. The y-axis represents gelatinolytic activity (%), the x-axis represents incubation time (h).

TABLE 3

| Incubation time (h) | Concentration of extract A (% w/v)/gelatinolytic activity as (%) | | | | |
|---|---|---|---|---|---|
| | 0.01 | 0.05 | 0.1 | 0.5 | 1 |
| 1 | 89 | 75 | 73 | 73 | 57 |
| 2 | 85 | 55 | 48 | 33 | 27 |
| 4 | 79 | 38 | 29 | 14 | 12 |
| 6 | 69 | 27 | 21 | 8 | 9 |
| 24 | 41 | 7 | 7 | 2 | 3 |

Under the experimental conditions selected, the peptide extract tested between 0.01 and 0.5% (w/v) has a dose-dependent and time-dependent antigelatinase/collagenase activity.

The aspecific inhibitor 1,10-phenanthroline was used in all the tests as a reference anti-MMP product. The results obtained were in accordance with those expected and validated the tests.

IV—Specific Anticollagenase Activity of the Lupin Peptides—extract A, on a Human Organotypic Model Skin aging is characterized, inter alia, by a modification of the cutaneous mechanical properties of the skin, subsequent to degradation of the collagen fibers of the dermis and of other macroproteins. This degradation involves endogenous collagenases (Grymes, R. A., Kronberger A. and Bauer E. A.—*Collagenases in disease*—in "*Connective Tissue Diseases of the skin*" Eds. Lapière C. M. and Krieg T., 1993, 69-85; G. Fischer and J. Voorhees "*Pathiophysiology of premature skin aging induced by ultraviolet light*" and "*Molecular mechanisms of photoaging and its prevention by retinoic acid: ultraviolet irradiation induces MAP kinase signal transduction cascades that induce A-1-regulated matrix metalloproteinases that degrade human skin in vivo*").

Products which have anticollagenase activity can be envisaged for combating the signs of skin aging.

The anticollagenase activity of a test product can be studied in vitro in an organotypic model of human skin. The principle of the test is as follows: application of purified collagenase to sections is accompanied by degradation of the endogenous collagen fibers. The collagen fibers are then stained with Masson trichrome. The digestion of the endogenous collagen fibers by the purified collagenase is evaluated qualitatively by morphological observation and quantitatively by image analysis. A product which has anticollagenase activity will partially or totally preserve the integrity of the collagen fibers placed in the presence of the enzyme.

The test products were stored at +4° C. until they were used.

Three dilutions were tested: 0.01; 0.1 and 1% (v/v).

Phosphoramidon, used as a reference product, came from SIGMA.

The purified collagenase (type III, fraction A) came from SIGMA.

The medium for incubating the human skin sections, subsequently named "vehicle" was 0.15 M Tris HCl buffer, pH 7.5, containing 0.01 M of calcium chloride.

The reagents, of analytical quality, came from CARLO ERBA, GIBCO or SIGMA, unless otherwise stated.

The skin sections were prepared from waste from an operation, recovered after abdominal plastic surgery. The individual was a 30-year-old woman. Skin explants 4 cm in diameter were prepared. They were placed on a cork support and frozen at −80° C. 6 µm-thick transverse sections were prepared using a cryomicrotome. They were fixed on glass slides and kept hydrated with the vehicle during the test.

The test samples were all taken up in ethanol before being diluted in the test buffer.

The final concentration of ethanol was maintained constant and equal to 0.1% (v/v) in the two weakest dilutions of the peptide extract (0.01 and 0.1% v/v);

It was maintained constant and equal to 1% (v/v) in the strongest dilution (1%, v/v).

"Ethanol controls" at 0.1 and 1% (v/v) were prepared.

The phosphoramidon was taken up directly in the vehicle.

The peptide extract was tested at 0.01; 0.1 and 1% (w/v).

The phosphoramidon was tested at $10^{-3}$ M.

The following samples were therefore present:

Extract: buffer; ethanol (0.1% v/v or 1% v/v); extracted enzyme (0.01; 0.1 and 1%, w/v);

Enzyme control: buffer; ethanol (0.1%, v/v); enzyme;

Ethanol control (without enzyme): buffer; ethanol (0.1% or 1%, v/v);

Ref. product: buffer; ethanol; enzyme; $10^{-3}$ M phosphoramidon.

The dilutions of the test products, of the ethanol and of the reference product were placed on to the skin sections, at 100 µl per section, and pre-incubated for 10 minutes at 37° C. Strips of filter paper (0.16 cm² surface area) soaked with vehicle alone (control without enzyme) or containing collagenase at 50 international units (IU)/ml (enzyme control) were then placed over the sections. The slides were placed in a humid chamber at 37° C. for three hours.

After incubation, the sections were rinsed with the incubation medium and stained with Masson trichrome. The activity of the enzyme in the presence and absence of the extract, of the ethanol or of the reference product was evaluated by microscopic observation and scored according to the following scheme:

0: zero enzymatic digestion

+: weak enzymatic digestion

++: average enzymatic digestion

+++: strong enzymatic digestion.

Photographs of the sections were taken.

The activity of the collagenase in the presence and absence of the test products, of the ethanol or of the reference product was evaluated by image analysis. The image of the stained sections was digitalized on a video screen; the image analysis software (IMAGENIA 2000, BIOCOM®) made it possible to calculate the surface area occupied by the intact collagen fibers. The results were expressed as a percentage of intact collagen fibers per optical field.

The percentage inhibition of the collagenase activity of the extracts at various concentrations of the ethanol and of the reference product was calculated using the following formulae:

For the reference product (directly taken up in the vehicle), the percentage inhibition is calculated using the following formula:

(% collagen fibers) ref product−(% collagen fibers) enzyme control×100(% collagen fibers) ethanol control−(% collagen fibers) enzyme control For the extracts diluted in the vehicle containing 0.1% (v/v) of ethanol, the percentage inhibition is calculated using the following formula:

(% collagen fibers) ref product−(% collagen fibers) enzyme control×100(% collagen fibers) ethanol control−(% collagen fibers) enzyme control For the extracts diluted in the vehicle containing 1% (v/v) of ethanol, the percentage inhibition is calculated using the following formula:

(% collagen fibers) ref product−(% collagen fibers) enzyme control×100/ (% collagen fibers) ethanol control−(% collagen fibers) enzyme control.

The anticollagenase activity of the extract at various concentrations was studied in an organotypic model of human skin.

In the absence of collagenase (vehicle control), the collagen fibers were intact. In the presence of collagenase (enzyme control), the collagen fibers were almost totally degraded. This result was expected and validated the test.

The phosphoramidon at $10^{-3}$ M, used as a reference product, inhibited the collagenase activity by 16%. This result was expected and completed the validation of the test.

The ethanol, used as an intermediate diluent of the test products was tested at 0.1 and 1% (v/v). It had no effect on the degradation of the collagen fibers by the collagenase.

The peptide extract tested at 0.01; 0.1 and 1% (w/v) inhibited the activity of the collagenase by 2, 24 and 65%, respectively. The morphological observation gave the same result.

In conclusion, under the experimental conditions selected, peptide extract A had considerable anticollagenase activity at low concentrations.

The results of inhibition, for the peptide extract, for the ethanol and for the phosphoramidon, on the digestion of dermal collagen fibers by collagenase are given in the table below:

TABLE 4

| Experimental condition | Concentration | Enzymatic digestion (morphological observation) | % inhibition of the collagenase activity (image analysis) |
| --- | --- | --- | --- |
| Vehicle control | — | 0 | — |
| Enzyme control | 50 IV/ml | +++ | 0 |
| Phosphoramidon (M) | $10^{-3}$ | + | + |
| Ethanol (%, v/v) | 0.1 | +++ | 0 |
|  | 1 | +++ | 0 |
| Peptide extract (%, v/v) | 0.01 | +++ | 2 |
|  | 0.1 | ++ | 24 |
|  | 1 | + | 65 |

0: zero enzymatic digestion
+: weak enzymatic digestion
++: average enzymatic digestion
+++: strong enzymatic digestion V—Antimetalloprotease MMP-2 and MMP-9 Activity of the Lupin Peptides—Extracts A, B and C MMP-2, or gelatinase A, and MMP-9, or gelatinase B, are metalloproteases which degrade specific components of the extracellular matrix: MMP-2 degrades gelatin (=denatured collagen), collagens I, IV, VII and XI, fibronectin, laminin and elastin; MMP-9 degrades gelatin, collagens IV, V and XIV and elastin. They play an important role in photoaging and in the proliferation of endothelial cells.

The anti-MMP-2 and anti-MMP-9 activity of the test products was measured in vitro in a biochemical model of the screening type, based on the use of a purified human MMP-2 and of a recombinant human MMP-9 and of the substrate for the latter, gelatin conjugated to fluorescein (EnzChek™ gelatinase/collagenase kit, MOLECULAR PROBES).

The MMP-2 purified from human fibrosarcoma came from BOEHRINGER MANNHEIM.

The recombinant human MMP-9 came from R&D SYSTEMS.

The DQ-gelatin purified from porcine skin and conjugated to fluorescein was supplied in the EnzChek™ gelatinase/collagenase kit (MOLECULAR PROBES).

The reaction buffer for studying the activity of MMP-2 (RBf1) consisted of 50 mM of Tris-HCl, 0.05% (w/v) of Triton X100 and 5 mM of $CaCl_2$, pH 7.5.

The reaction buffer for studying the activity of MMP-9 (RBf2) consisted of 50 mM of Tris-HCl, 0.05% (w/v) of Brij 35 and 5 mM of $CaCl_2$, pH 7.4.

Preparation of the Test Products and of the Reference Product 1,10-Phenanthroline was solubilized in the reaction buffers RBf1 and RBf2. It was tested at 8 and 80 µg/ml.

Peptide extracts A, B and C were solubilized in the reaction buffers RBf1 and RBf2. They were tested at 0.01; 0.1 and 1% (w/v).

MMP-2

Before being used, the MMP-2 was activated by incubation for 30 minutes at 37° C. in the presence of APMA diluted to 2.5 mM in the buffer RBf1.

The dilutions of the test products or of the reference product were incubated with the DQ-gelatin, diluted to 25 µg/ml, and the activated MMP-2, diluted to 1.25 µg/ml, for 24 hours at 37° C.

A control corresponding to the "MMP-2+DQ-gelatin" mixture, was incubated in parallel.

For each experimental condition, samples, subsequently named "samples without enzyme", were incubated in the presence of DQ-gelatin and in the absence of activated MMP-2. These samples made it possible to measure the interference of the test products with the method for evaluating the effects (fluorimetry).

Each experimental condition was performed in triplicate.

MMP-9

The dilutions of the test products or of the reference product were incubated with the DQ-gelatin, diluted to 25 µg/ml, and the MMP-9, diluted to 0.25 µg/ml, for 24 hours at 37° C.

A control corresponding to the "MMP-9+DQ-gelatin" mixture, was incubated in parallel.

For each experimental condition, samples, subsequently named "samples without enzyme", were incubated in the presence of DQ-gelatin and in the absence of MMP-9. These samples made it possible to measure the interference of the test products with the method for evaluating the effects (fluorimetry).

Each experimental condition was performed in triplicate.

After 24 hours, the signal corresponding to the degradation of the DQ-gelatin was measured by fluorimetry (excitation: 485 nm and emission: 595 nm). For each sample, the value obtained for the "samples without enzyme" was subtracted.

The results were expressed as fluorescence units per sample and as percentage variation relative to the control group.

The groups of data (control group and treated groups) were compared by onefactor analysis of variance (ANOVA 1, $p < 0.05$), followed by a Dunnett's test.

The results are given below:

V.1 - Anti-MMP-2 activity

| Peptide extract | Control | MMP-2 activity (as %) (1)/ Concentration (% v/v) of 10% by weight solution of peptide extract | | |
|---|---|---|---|---|
| | | 0.01 | 0.1 | 1 |
| C | 100 | 119 | 111 | 43 |
| A | 100 | 152 | 151 | 68 |
| B | 100 | 110 | 98 | 77 |

(1) Activity expressed relative to the control group in the absence of MMP-2 inhibitor Conclusion:
  The 10% by weight solution of extract of lupin C, tested at 0.01 and 0.1% (v/v) has no anti-MMP-2 activity. When tested at 1% (v/v), it inhibits the MMP-2 by 57%.
  The 10% by weight solution of extract of lupin A, tested at 0.01 to 0.1% (v/v) has no anti-MMP-2 activity. When tested at 1% (v/v), it inhibits the MMP-2 by 32%.
  The 10% by weight solution of extract B, tested at 1%, inhibits the MMP-2 by 23%.
  The phenanthroline, tested at 8 and 80 µg/ml, inhibits the activity of the MMP-2 by 32 and 73%, respectively. This result, which was expected, validates the test.

V.2 - Anti-MMP-9 activity

| Peptide extract | Control | MMP-9 activity (as %) (1)/ Concentration (% v/v) of 10% by weight solution of peptide extract | | |
|---|---|---|---|---|
| | | 0.01 | 0.1 | 1 |
| A | 100 | 143 | 143 | 61 |
| B | 100 | 146 | 129 | 27 |

(1) Activity expressed relative to the control group in the absence of MMP-9 inhibitor Conclusion:
  The 10% by weight solution of extract of lupin A, tested at 0.01 and 0.1% (v/v) has no anti-MMP-9 activity. When tested at 1% (v/v), it inhibits the MMP-9 by 39%.
  The 10% by weight solution of extract of lupin B, tested at 0.01 and 0.1% (v/v) has no anti-MMP-9 activity. When tested at 1% (v/v), it inhibits the MMP-9 by 73%.
  The phenanthroline, tested at 8 and 80 µg/ml, inhibits the activity of the MMP-9 by 80 and 76%, respectively. This result, which was expected, validates the test.

VI—Evaluation of the Effect of the Lupin Peptides on the Amount of MMP-1-9 and -3 in Human Fibroblasts Irradiated with UVA Rays The study was carried out on human dermal fibroblasts in monolayer culture. The cells were pre-incubated for 1 hour at 37° C. in the presence of the reference products and of the test product. Then, the cells were irradiated with a single dose of 10 J/cm² of UVA, in the presence of the product to be tested and of the reference products.

Immediately after irradiation, the cells were incubated for 48 h at 37° C., still in the presence of the product to be tested and of the reference products.

The various MMPs are tested in the culture media using specific ELISA kits (Amersham).

Reference Products and Test Product
  1,10-Phenanthroline, which is a nonspecific inhibitor of MMPs, and was tested at 80 µg/ml, was used as a reference product.
  A 10 µg/ml retinoic acid+10 ng/ml EGF mixture was used for its abilities to induce TIMP1 (TIMP1, Tissue Inhibitor of MMP, physiological inhibitor of MMPs).
  A stock solution containing 10% (w/v) of lupin peptides was prepared in deionized water. Using this solution, dilutions were prepared in the fibroblast culture medium. The peptide extract of lupin was tested at 0.5; 1 and 2% (v/v).
  Irradiated and nonirradiated control cultures were incubated in parallel, in the absence of the reference products and of the test product.

Processing of Data
  The groups of data (control group and treated groups) were compared by one-factor analysis of variance (ANOVA 1, $p > 0.05$), followed by a Dunnett's test. The effects of the reference products and of the test product were thus compared to that obtained in the "irradiated cells" group.

Results:
  They are given in the table below and the results are expressed as % relative to the "irradiated cells" group.

| | Production of MMP (as %) | | | | |
|---|---|---|---|---|---|
| | Control | Irradiated | Irradiated cells + lupin peptides (%, v/v) | | |
| | cells | cells | 0.5 | 1 | 2 |
| MMP-1 | 24 | 100 | 4 | 3 | 3 |
| MMP-9 | 41 | 100 | 17 | 2 | 0 |
| MMP-3 | 88 | 100 | 3 | 0 | 2 |

Conclusions:
  The 1,10-phenanthroline, tested at 80 µg/ml, inhibited by 99% the secretion of MMP-1, by 92% the secretion of MMP-9 and by 97% the secretion of MMP-3, by the irradiated fibroblasts.
  The 10 µM retinoic acid+10 ng/ml EGF mixture inhibited by 58% the secretion of MMP-1, by 67% the secretion of MMP-9 and by 44% the secretion of MNP-3, by the irradiated fibroblasts.
  These results were expected and validated the reactivity of the test system.
  The irradiation at the dose of 10 J/cm² increased by a factor of 4.10; 2.42 and 1.13, the respective amounts of MMP-1, -9 and -3 secreted by the fibroblasts. These results were expected and validated the test system with regard to the induction of MMP-1, -9 and -3 by UVA radiation.
  The peptide extract of lupin, tested at 0.5, 1 and 2% (v/v), decreased by 96, 97 and 97%, respectively, the amount of MMP-1 secreted by the fibroblasts ($p < 0.05$).
  The peptide extract of lupin, tested at 0.5, 1 and 2%, decreased by 83, 98 and 100%, respectively, the amount of MMP-9 secreted by the fibroblasts ($p < 0.05$).
  The peptide extract of lupin, tested at 0.5, 1 and 2%, decreased by 97, 100 and 98%, respectively, the amount of MMP-3 secreted by the fibroblasts ($p < 0.05$).
  Thus, under the experimental conditions selected, the peptide extract of lupin has considerable inhibitory properties with respect to the production of MMP-1, -9 and -3 by UVA-irradiated human dermal fibroblasts.

VII—Examples of Formulae for Topical Use

The percentages are expressed as total weight of the composition. The peptide extract of lupin is used in the form of a 10% by weight aqueous solution according to the invention or of a lyophilized powder named powder form peptide extract.

1. Cream Acting Against Red Blotches, for Normal Skin

|  |  |
| --- | --- |
| Water | q.s. for 100.000 |
| Pentaerythrityl tetraoctanoate | 15.0 to 5.0 |
| Glyceryl stearate | 10.0 to 2.0 |
| Isodecyl neopentanoate | 10.0 to 2.0 |
| Propylene glycol | 1.0 to 3.0 |
| Dextrin | 1.0 to 3.0 |
| Cyclomethicone | 1.0 to 3.0 |
| Soybean (soybean glycine) extract | 0.1 to 10.0 |
| Peptide extract of lupin (10% aqueous solution) | 0.1 to 10.0 |
| Titanium dioxide | 1.0 to 3.0 |
| Candelilla wax (Euphorbia Cerifora) | 1.0 to 3.0 |
| Rice starch (Oriza Sativa) | 1.0 to 3.0 |
| Unsaponifiable soybean (soybean glycine) oil | 0.01 to 10.0 |
| Caprylic/capric acid triglycerides | 0.5 to 5.0 |
| PEG-100 stearate | 0.5 to 5.0 |
| Sophora Japonica extract | 0.1 to 10.00 |
| Stearic acid | 0.5 to 1.0 |
| Tocopheryl acetate | 0.1 to 1.0 |
| Phenoxyethanol | 0.1 to 1.0 |
| CI 77891 | 0.1 to 1.0 |
| Xanthan gum | 0.1 to 0.5 |
| Dimethiconol | 0.1 to 0.5 |
| Polyacrylamide | 0.1 to 0.5 |
| Mica | 0.1 to 0.5 |
| Ceteareth-20 | 0.1 to 0.5 |
| Chlorphenesine | 0.1 to 0.5 |
| Carbomer | 0.1 to 0.5 |
| Octyl palmitate | 0.1 to 0.5 |
| Tromethamine | 0.1 to 0.5 |
| Beeswax | 0.1 to 0.5 |
| C13-14 Isoparaffin | 0.1 to 0.5 |
| DEA cetyl phosphate | 0.1 to 0.5 |
| Cetyl alcohol | 0.1 to 0.5 |
| Glucose | 0.1 to 0.5 |
| Fragrance | 0.1 to 0.5 |
| Disodium EDTA | 0.1 to 0.5 |

2. Antiaging Preventive Cream

|  | % |
| --- | --- |
| Water | q.s. for 100.00000 |
| Pentaerythrityl tetraoctanoate | 3.0 to 15.0 |
| Isodecyl neopentanoate | 3.0 to 15.0 |
| Squalane | 1.0 to 10.0 |
| Dextrin | 1.0 to 10.0 |
| Cyclomethicone | 1.0 to 10.0 |
| Cetearyl alcohol | 1.0 to 10.0 |
| Peptide extract of lupin (10% aqueous solution) | 0.1 to 10.0 |
| Ascorbyl glucoside | 0.1 to 10.0 |
| Glycerol | 1.0 to 10.0 |
| Laureth-23 | 1.0 to 10.0 |
| Myristyl myristate | 1.0 to 10.0 |
| Cyclopentasiloxane | 1.0 to 10.0 |
| Nylon-6 | 1.0 to 10.0 |
| Avocado furan | 0.01 to 10.0 |
| Phenoxyethanol | 0.1 to 1.0 |
| Cetearyl glucoside | 0.1 to 1.0 |
| Fragrance | 0.1 to 1.0 |
| Beeswax | 0.1 to 1.0 |
| Methylparaben | 0.1 to 0.5 |
| Sodium citrate | 0.1 to 0.5 |
| Dimethiconol | 0.1 to 0.5 |
| Glyceryl stearate | 0.1 to 0.5 |
| Disodium EDTA | 0.1 to 0.5 |
| Propylparabene | 0.1 to 0.5 |
| Sodium hydroxide | 0.1 to 0.5 |
| Acrylate/C10-30 alkyl acrylate crosspolymers | 0.1 to 0.5 |
| Xantham gum | 0.1 to 0.5 |
| Glucose | 0.1 to 0.5 |

3. Antiaging Cream for Mature Skin

|  |  |
| --- | --- |
| Water | q.s. for 100.0000 |
| Pentaerythrityl tetraoctanoate | 1.0 to 10.0 |
| Isodecyl neopentanoate | 1.0 to 10.0 |
| Hydrogenated cocoglycerides | 1.0 to 10.0 |
| Simmondsia Chinensis (jojoba) seed oil | 1.0 to 10.0 |
| Squalane | 1.0 to 10.0 |
| Glycerol | 1.0 to 10.0 |
| Cyclomethicone | 1.0 to 5.0 |
| Cetearyl alcohol | 1.0 to 5.0 |
| Myristyl myristate | 1.0 to 5.0 |
| Laureth-23 | 1.0 to 5.0 |
| Silica | 1.0 to 5.0 |
| Peptide extract of lupin (10% aqueous solution) | 0.1 to 10.0 |
| Sclerotium gum | 0.1 to 1.0 |
| Avocado furan | 0.01 to 10.0 |
| Salicylic acid | 0.1 to 10.0 |
| Beeswax | 0.1 to 10.0 |
| Polyacrylamide | 0.1 to 1.0 |
| Phenoxyethanol | 0.1 to 1.0 |
| Glyceryl stearate | 0.1 to 1.0 |
| Retinol palmitate | 0.01 to 5.0 |
| Cetearyl glucoside | 0.01 to 5.0 |
| Nylon-6 | 0.01 to 5.0 |
| Titanium dioxide | 0.01 to 5.0 |
| Fragrance | 0.1 to 5.0 |
| Tocopheryl acetate | 0.1 to 5.0 |
| Potassium sorbate | 0.1 to 5.0 |
| Methylparabene | 0.1 to 5.0 |
| C13-14 Isoparaffin | 0.1 to 5.0 |
| CI 77891 | 0.1 to 5.0 |
| Dimethiconol | 0.1 to 5.0 |
| Propylparabene | 0.1 to 5.0 |
| Sodium hydroxide | 0.1 to 5.0 |
| Laureth-7 | 0.1 to 5.0 |
| Cetearyl alcohol | 0.1 to 5.0 |
| Cetyl palmitate | 0.1 to 5.0 |
| Cocoglycerides | 0.1 to 5.0 |
| Disodium EDTA | 0.1 to 0.5 |
| CI 77491 | 0.1 to 0.5 |
| Citric acid | 0.1 to 0.5 |

4. Cream Acting Against Red Blotches, for Dry to Very Dry Skin

|  |  |
| --- | --- |
| Water | q.s. for 100.00000 |
| Petrolatum | 1.0 to 10.0 |
| Hydrogenated cocoglycerides | 1.0 to 10.0 |
| Isodecyl neopentanoate | 1.0 to 10.0 |
| Simmondsia Chinensis (jojoba) oil | 1.0 to 2.0 |
| Butylene glycol | 1.0 to 5.0 |
| Cetearyl alcohol | 1.0 to 5.0 |
| Glycerol | 1.0 to 10.0 |
| Squalane | 1.0 to 10.0 |
| Peptide extract of lupin | 0.1 to 10.0 |

-continued

| | |
|---|---|
| (10% aqueous solution) | |
| Laureth-23 | 1.0 to 10.0 |
| Titanium dioxide | 1.0 to 10.0 |
| Unsaponifiable soybean glycine (soybean) oil | 0.1 to 10.0 |
| Caprylic/capric acid triglycerides | 1.0 to 5.0 |
| Phenoxyethanol | 0.1 to 1.0 |
| Cetearyl glucoside | 0.1 to 1.0 |
| Soybean seed extract | 0.1 to 10.0 |
| Fragrance | 0.1 to 1.0 |
| Sophora Japonica | 0.1 to 10.0 |
| Tocopheryl acetate | 0.1 to 1.0 |
| Candelilla wax | 0.1 to 1.0 |
| CI 77891 | 0.1 to 0.5 |
| Methylparabene | 0.1 to 0.5 |
| Mica | 0.1 to 0.5 |
| Propylparabene | 0.1 to 0.5 |
| Ethylhexyl palmitate | 0.1 to 0.5 |
| Chlorphenesine | 0.1 to 0.3 |
| Acrylate/C10-30 alkyl acrylate crosspolymers | 0.1 to 0.3 |
| Xantham gum | 0.1 to 0.3 |
| Disodium EDTA | 0.1 to 0.3 |
| Sodium hydroxide | 0.1 to 0.3 |

VIII—Examples of Mouthwash Solutions

The percentages are expressed as total weight of the composition. The peptide extract of lupin is used in the form of a 10% by weight aqueous solution according to the invention or of a lyophilized powder named powder form peptide extract.

1. 10% Aqueous Solution Peptide Extract of Lupin+Antiseptic (Triclosan)+Antiplaque Agent (Gantrez S97BF®)

| | |
|---|---|
| Peptide extract of lupin | 2 |
| Ethyl alcohol | 10 |
| Glycerol | 10 |
| Hydrogenated castor oil ethoxylated at 40 mol EO (Cremophor co410) | 0.5 |
| Poly(methyl vinyl ether/maleic acid) (Gantrez S97BF ®) | 0.2 |
| Sodium hydroxide | 0.15 |
| Sodium fluoride | 0.05 |
| Cinnamon-mint flavoring | 0.1 |
| Triclosan | 0.03 |
| Zinc chloride | 0.01 |
| Sodium saccharin | 0.01 |
| Coloring C.I. 16255 (E 124) | 0.0025 |
| Purified water | q.s. for 100 |

2. 10% Aqueous Solution Peptide Extract of Lupin+Antiseptic

| | |
|---|---|
| Peptide extract of lupin | 2 |
| Ethyl alcohol | 10 |
| Glycerol | 10 |
| Hydrogenated castor oil ethoxylated at 40 mol EO (Cremophor co410) | 0.3 |
| Sodium fluoride | 0.05 |
| Cinnamon-mint flavoring | 0.1 |
| Triclosan | 0.03 |
| Zinc chloride | 0.01 |
| Sodium saccharin | 0.01 |
| Coloring C.I. 16255 (E 124) | 0.0025 |
| Purified water | q.s. for 100 |

3. Powder Form Peptide Extract of Lupin+Antiseptic (cetylpyridinium chloride)

| | |
|---|---|
| Peptide extract of lupin | 1 |
| Ethyl alcohol | 10 |
| Glycerol | 8 |
| Hydrogenated castor oil ethoxylated at 40 mol EO (Cremophor co410) | 0.1 |
| Sodium fluoride | 0.05 |
| Cinnamon-mint flavoring | 0.1 |
| Cetylpyridinium chloride | 0.05 |
| Zinc chloride | 0.01 |
| Sodium saccharin | 0.01 |
| Coloring C.I. 16255 (E 124) | 0.0025 |
| Purified water | q.s. for 100 |

IX—Examples of Toothpastes

The percentages are expressed as total weight of the composition. The peptide extract of lupin is used in the form of a 10% by weight aqueous solution according to the invention or of a lyophilized powder named powder form peptide extract.

1. Powder form Peptide Extract of Lupin+Fluorides

| | |
|---|---|
| Peptide extract of lupin | 1 |
| Sodium monofluorophosphate | 0.75 |
| Sodium fluoride | 0.10 |
| 70% sorbitol | 35 |
| Synthetic silica with strong abrasive power | 13 |
| Synthetic silica with weak abrasive power | 5 |
| Sodium carboxymethylcellulose | 1.6 |
| Sodium lauryl sulfate | 1 |
| Mentholated flavoring | 0.85 |
| Titanium oxide | 0.5 |
| Sodium hydroxide lye | 0.5 |
| Sodium cyclamate | 0.3 |
| Menthol | 0.15 |
| Sodium saccharin | 0.07 |
| Purified water | q.s. for 100 |

2. 10% Aqueous Solution Peptide Extract of Lupin +fluorides

| | |
|---|---|
| Peptide extract of lupin | 2 |
| Sodium monofluorophosphate | 0.75 |
| Sodium fluoride | 0.10 |
| 70% sorbitol | 35 |
| Synthetic silica with strong abrasive power | 13 |
| Synthetic silica with weak abrasive power | 5 |
| Sodium carboxymethylcellulose | 1.6 |
| Sodium lauryl sulfate | 1 |
| Mentholated flavoring | 0.85 |
| Titanium oxide | 0.5 |
| Sodium hydroxide lye | 0.5 |
| Sodium cyclamate | 0.3 |
| Menthol | 0.15 |
| Sodium saccharin | 0.07 |
| Purified water | q.s. for 100 |

BRIEF DESCRIPTION OF THE FIGURE(S)

FIG. 1 shows the anticollagenase and antigelatinolytic activity of the lupin peptides—Extract A, in vitro.

The invention claimed is:

1. A composition comprising a peptide extract of a lupin, wherein said peptide extract is lipid-depleted and contains at least 50% of peptides relative to dry extract, the composition has a sugar content lower than 1% relative to dry extract, and said peptides have a molecular weight of less than 10,000 Daltons.

2. The composition of claim 1, wherein the peptide extract of lupin has metalloprotease inhibiting activity.

3. The composition of claim 1, wherein the peptide extract of lupin has collagenase inhibiting activity.

4. The composition of claim 1, wherein the peptide extract of lupin has gelatinase inhibiting activity.

5. The composition of claim 1, wherein the peptide extract of lupin has stromelysin inhibiting activity.

6. The composition of claim 1, wherein the peptide extract of lupin is a peptide extract of sweet white lupi (*lupinus albus*).

7. The composition of claim 6, wherein the peptide extract of sweet white lupin (*lupinus albus*) is a peptide extract of Ares variety of sweet white lupin (*lupinus albus*).

8. The composition of claim 1, wherein peptides of the peptide extract of lupin have a molecular weight of less than 10,000 Daltons.

9. The composition of claim 1, wherein the peptide extract of lupin has the following amino acid composition, expressed as a percentage by weight relative to the total weight of amino acids:

| Amino Acids | % by Weight/Total Weight of Amino Acids |
|---|---|
| ASP | 11.3 |
| GLU | 23.2 |
| SER | 5.1 |
| HIS | 1.7 |
| GLY | 3.4 |
| THR | 3.2 |
| ALA | 2.8 |
| ARG | 10.3 |
| TYR | 6.1 |
| CYS-CYS | 2.4 |
| VAL | 3.8 |
| MET | 0.2 |
| PHE | 7.0 |
| ILE | 3.3 |
| LEU | 7.9 |
| LYS | 3.7 |
| PRO | 4.4. |

10. The composition of claim 1, further comprising a physiologically acceptable inert vehicle.

11. A formulation for oral administration in the form of a tablet, a capsule or an ointment, wherein said formulation contains the composition according to claim 1.

12. A method for producing the composition of claim 1, comprising:
(a) extracting a protein fraction from a lupin to provide a peptide extract,
(b) hydrolyzing the peptide extract, and
(c) recovering the hydrolyzed peptide extract; wherein step (a) comprises
(i) preparing a lipid-free, ground lupin meal or a micronized lupin flour optionally containing lipid, and
(ii) extracting soluble protein and saccharide fractions from said lupin meal or flour, or precipitating the proteins as the isoelectric point.

13. The method of claim 12 further wherein (b) is carried out enzymatically.

14. The method of claim 13, wherein (a) is followed by ultrafiltration of the protein fraction prior to (b).

15. The method of claim 12, wherein (b) is followed by ultrafiltration of the hydrolyzed peptide extract of lupin.

16. A method of treating a condition or disease linked to degradation of collagen or another extracellular support macroprotein in a mammal, comprising orally administering a composition comprising an effective amount of the peptide extract of lupin according to claim 1 to the mammal.

17. The method of claim 16, wherein the condition or disease is a skin lesion due to aging, or a skin lesion caused by solar radiation, tobacco use, pollution or stress.

18. The method of claim 16, wherein the composition inhibits metalloprotease activity when administered to the subject.

19. The method of claim 16, wherein the composition inhibits collagenase activity, gelatinase activity or stromelysin activity when administered to the subject.

20. The method of claim 16, wherein the peptide extract of lupin is a hydrolyzed extract of a sweet white lupin.

21. The method of claim 16, wherein the hydrolyzed peptide extract of the sweet white lupin is a hydrolyzed extract of an Ares variety of sweet white lupin.

22. The method of claim 16, wherein the mammal is a human.

23. A method of inhibiting metalloprotease activity in a mammal, comprising orally administering an effective amount of the peptide extract of lupin according to claim 1 to the mammal.

24. The method of claim 23, wherein the metalloprotease activity is collagenase activity, gelatinase activity or stromelysin activity.

25. The method of claim 23, wherein the peptide extract of lupin is a hydrolyzed extract of a sweet white lupin or a hydrolyzed extract of an Ares variety of sweet white lupin.

26. The method of claim 23, wherein the mammal is a human.

* * * * *

UNITED STATES PATENT AND TRADEMARK OFFICE
CERTIFICATE OF CORRECTION

| | |
|---|---|
| PATENT NO. | : 7,638,149 B2 |
| APPLICATION NO. | : 10/985988 |
| DATED | : December 29, 2009 |
| INVENTOR(S) | : Msika et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

Signed and Sealed this

Ninth Day of November, 2010

David J. Kappos
*Director of the United States Patent and Trademark Office*